(12) United States Patent
Yoo et al.

(10) Patent No.: US 8,261,389 B2
(45) Date of Patent: Sep. 11, 2012

(54) CLOTH TREATING APPARATUS AND CONTROLLING METHOD THEREOF

(75) Inventors: Hea Kyung Yoo, Seoul (KR); Sog Kie Hong, Seoul (KR); Dong Won Kim, Seoul (KR); Jong Seok Kim, Seoul (KR); Dae Yun Park, Seoul (KR)

(73) Assignee: LG Electronics, Inc., Seoul (KR)

( * ) Notice: Subject to any disclaimer, the term of this patent is extended or adjusted under 35 U.S.C. 154(b) by 800 days.

(21) Appl. No.: 12/382,904

(22) Filed: Mar. 26, 2009

(65) Prior Publication Data

US 2009/0241268 A1 Oct. 1, 2009

(30) Foreign Application Priority Data

Apr. 1, 2008 (KR) .................. 10-2008-0030337

(51) Int. Cl.
*D06B 19/00* (2006.01)
*D06B 1/00* (2006.01)
(52) U.S. Cl. .......................... 8/149.3; 34/493
(58) Field of Classification Search .............. 8/149.1, 8/149.2, 149.3, 158, 159; 34/321, 443, 471, 34/493, 494, 497
See application file for complete search history.

(56) References Cited

U.S. PATENT DOCUMENTS

| 6,615,850 B1 | 9/2003 | Hornung |
| 2006/0251540 A1 | 11/2006 | Benning et al. |
| 2007/0169282 A1 | 7/2007 | Kim |
| 2008/0040871 A1 | 2/2008 | Wong et al. |
| 2008/0092928 A1* | 4/2008 | Wong et al. ............ 134/30 |
| 2008/0276382 A1* | 11/2008 | Benne et al. ........... 8/158 |

FOREIGN PATENT DOCUMENTS

| WO | WO 2006101361 A1 * | 9/2006 |
| WO | WO 2008/004802 | 1/2008 |
| WO | WO 2008/030051 | 3/2008 |
| WO | WO 2008/030066 | 3/2008 |

* cited by examiner

*Primary Examiner* — Joseph L Perrin
(74) *Attorney, Agent, or Firm* — McKenna Long & Aldridge LLP

(57) ABSTRACT

A control method of the same are disclosed. A control method of a laundry treating machine comprising an accommodating space receiving laundry therein, the control method includes selecting one of at least two sanitary courses to sanitize objects, and supplying steam to the objects, with controlling a temperature of the accommodating space and a steam supplying time to maintain a temperature of the object to be at a predetermined sanitary standard temperature or higher for a predetermined sanitary standard time according to the selected course. According to the control method of the present invention, steam may be supplied appropriately according to the load amount of the laundry treating machine such that damage of laundry fabric may be prevented, sanitizing, or sterilizing the laundry.

12 Claims, 6 Drawing Sheets

CLOTH TREATING APPARATUS AND CONTROLLING METHOD THEREOF

CROSS REFERENCE TO RELATED APPLICATION

This application claims the benefit of the Patent Korean Application No. 10-2008-0030337, filed on Apr. 1, 2008, which is hereby incorporated by reference as if fully set forth herein.

BACKGROUND OF THE DISCLOSURE

1. Field of the Disclosure

The present invention relates to a cloth treating apparatus. More particularly, the present invention relates to a control method of a cloth treating apparatus capable of supplying steam to laundry received therein appropriately according to load of laundry to sterilize or sanitize laundry.

2. Discussion of the Related Art

Cloth treating apparatuses typically include washing machines, dryers, and laundry machines having washing and drying functions. In recent years, refreshers have been developed, which are capable of refreshing clothes and substantially have improved the standard of living.

The cloth treating apparatus also have various functions beyond the conventional ones. In recent years, laundry treating machines capable of selectively supplying steam to sanitize or sterilize laundry have also been developed.

If the temperature for the sterilization or sanitization is preset too high in the laundry treating machine capable of spraying steam, the fabric of the laundry to be treated might be damaged. For example, if the temperature of the steam is too high deformation, shrinkage or discoloration may result. On the other hand, if the temperature is preset too low in the laundry treating machine, the sterilization/sanitization process may be incomplete.

The present invention is developed to solve the above problems and to provide a control method for a laundry treating machine that is capable of supplying steam appropriately according to load of laundry received therein to prevent energy waste.

SUMMARY OF THE DISCLOSURE

Accordingly, the present invention is directed to a laundry treating machine and a control method of the same.

Additional advantages and features of the disclosure will be set forth in part in the description which follows and in part will become apparent to those having ordinary skill in the art upon examination of the following or may be learned from practice of the invention. The advantages and features of the invention may be realized and attained by the structure particularly pointed out in the written description and claims hereof as well as the appended drawings.

To achieve these advantages and features, and in accordance with the purpose of the invention, as embodied and broadly described herein, a control method of a laundry treating machine comprising an accommodating space receiving laundry therein, the control method includes selecting one of at least two sanitary courses to sanitize objects; and supplying steam to the objects, with controlling a temperature of the accommodating space and a steam supplying time to maintain a temperature of the object to be at a predetermined sanitary standard temperature or higher for a predetermined sanitary standard time according to the selected course.

A user may select one of preset sanitary courses or the kind of the object.

The at least two courses may include a first course and a second course in which at least of a predetermined maximum temperature of the accommodating space, a predetermined minimum temperature of the accommodating space and a steam supplying time may be different from corresponding at least one in the first course.

A load amount of the objects in the first course may be different from a load amount of the objects in the second course.

The load amount of the object in the first course may be substantially larger than the load amount of the object in the second course and the predetermined maximum temperature of the accommodating space in the first course may be substantially higher than the predetermined maximum temperature of the accommodating space in the second course.

The steam supplying time in the first course may be substantially longer than the steam supplying time in the second course.

The steam supplying time in the first course may be controlled according to the predetermined maximum temperature of the accommodating space and the steam supplying time in the second course may be controlled according to the predetermined minimum temperature of the accommodating space.

The first course may include at least two courses configured of A and B courses according to the load amount of the objects, and a heater generating steam may be turned off, if the temperature of the accommodating space reaches the predetermined maximum temperature for the first time in case that the A course is selected, and the heater may be turned off, if the temperature of the accommodating space reaches the predetermined maximum temperature for the second time in case that the B course is selected.

If the second courses is selected, the temperature of the accommodating space may be feedback-controlled to be maintained between the predetermined maximum temperature and the predetermined minimum temperature of the accommodating space and a heater generating steam may be turned off if the time period for which the temperature of the accommodating space is maintained at the predetermined minimum temperature of the accommodating space or higher is the sanitary standard time or longer.

If the first course is selected, the temperature of the accommodating space may be controlled according to the predetermined maximum temperature of the accommodating space and if the first course is selected, the temperature of the accommodating space may be feedback-controlled.

The temperature of the accommodating space may be controlled by turning on or off a heater generating steam.

The first course includes at least two courses configured of A and B courses, and the heater may be turned off, if the temperature of the accommodating space reaches the predetermined maximum temperature for the first time in case that the A course is selected, and the heater may be turned off, if the temperature of the accommodating space reaches the predetermined maximum temperature for the second time in case that the B course is selected.

If the second course is selected, the temperature of the accommodating space may be feedback-controlled to be maintained between the predetermined maximum temperature and the predetermined minimum temperature of the accommodating space, and the heater may be turned off, if the time period for which the temperature of the accommodating space is maintained at the predetermined minimum temperature or higher is the sanitary standard time or longer.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the disclosure and are incorporated in and constitute a part of this application, illustrate embodiment(s) of the disclosure and together with the description serve to explain the principle of the disclosure. In the drawings:

FIG. 1 is a front view illustrating a cloth treating apparatus which a control method according to an exemplary embodiment of the present invention can be applicable to;

DESCRIPTION OF THE EMBODIMENTS

Reference will now be made in detail to the specific embodiments of the present invention, examples of which are illustrated in the accompanying drawings. Wherever possible, the same reference numbers will be used throughout the drawings to refer to the same or like parts.

Figure 1:
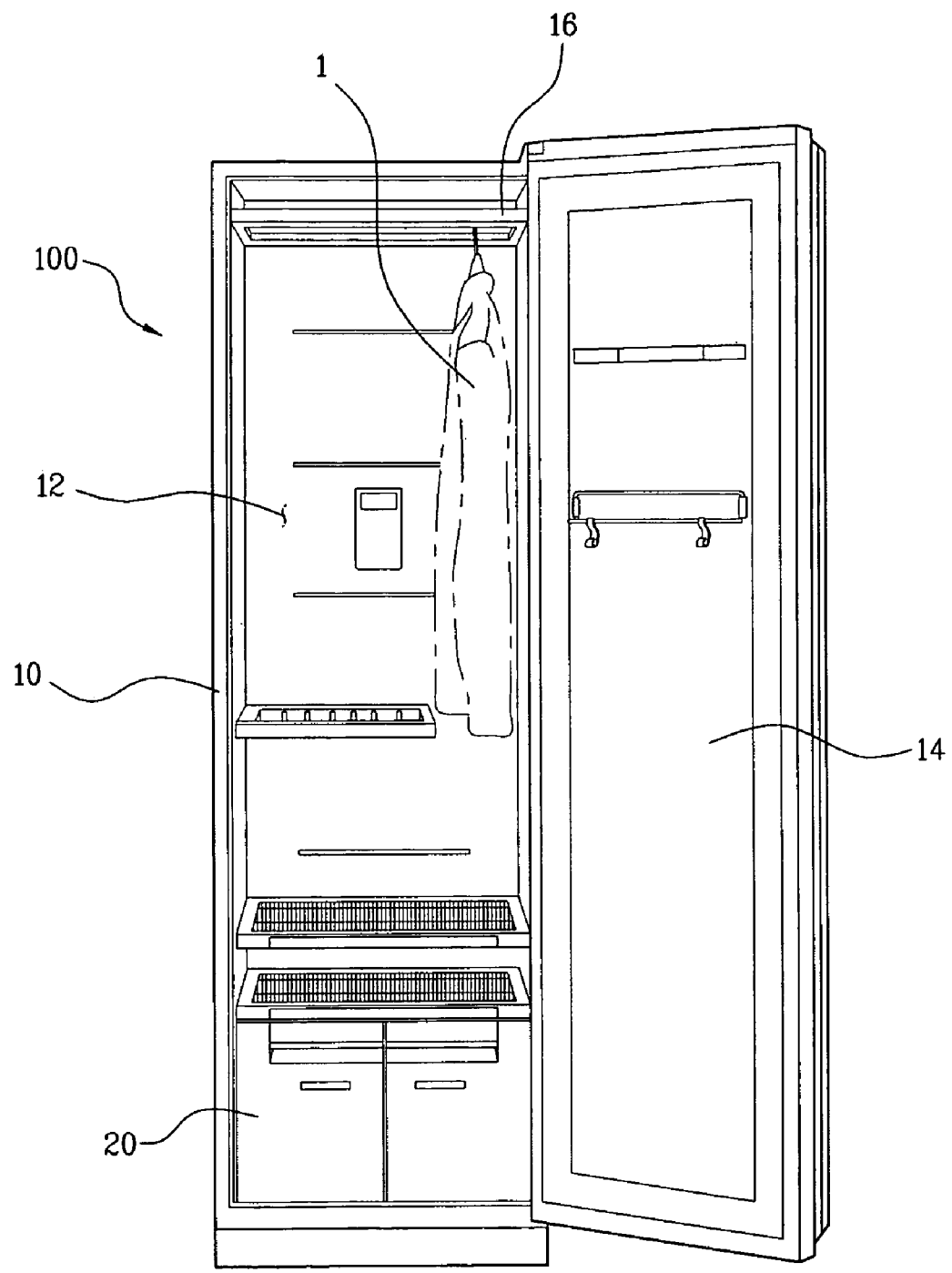

FIG. 1 is a front view illustrating a laundry treating machine according to an exemplary embodiment of the present invention. The disclosure of the exemplary embodiment of the invention presents a refresher refreshing clothes by using steam as a cloth treating machine. The present invention, however, is not limited to refreshers and it may be applicable to other kinds of laundry treating apparatus capable of supplying steam to laundry. For example, washing machines, dryers, and laundry machines having washing and drying functions may also be applicable to the present invention. The term "laundry" here means any piece of clothing, sheets, towels, drapes, shoes, or any object which maybe refreshed or sanitized. A configuration of the laundry treating apparatus will now be described and a control method of the same will follow.

Figure 2:
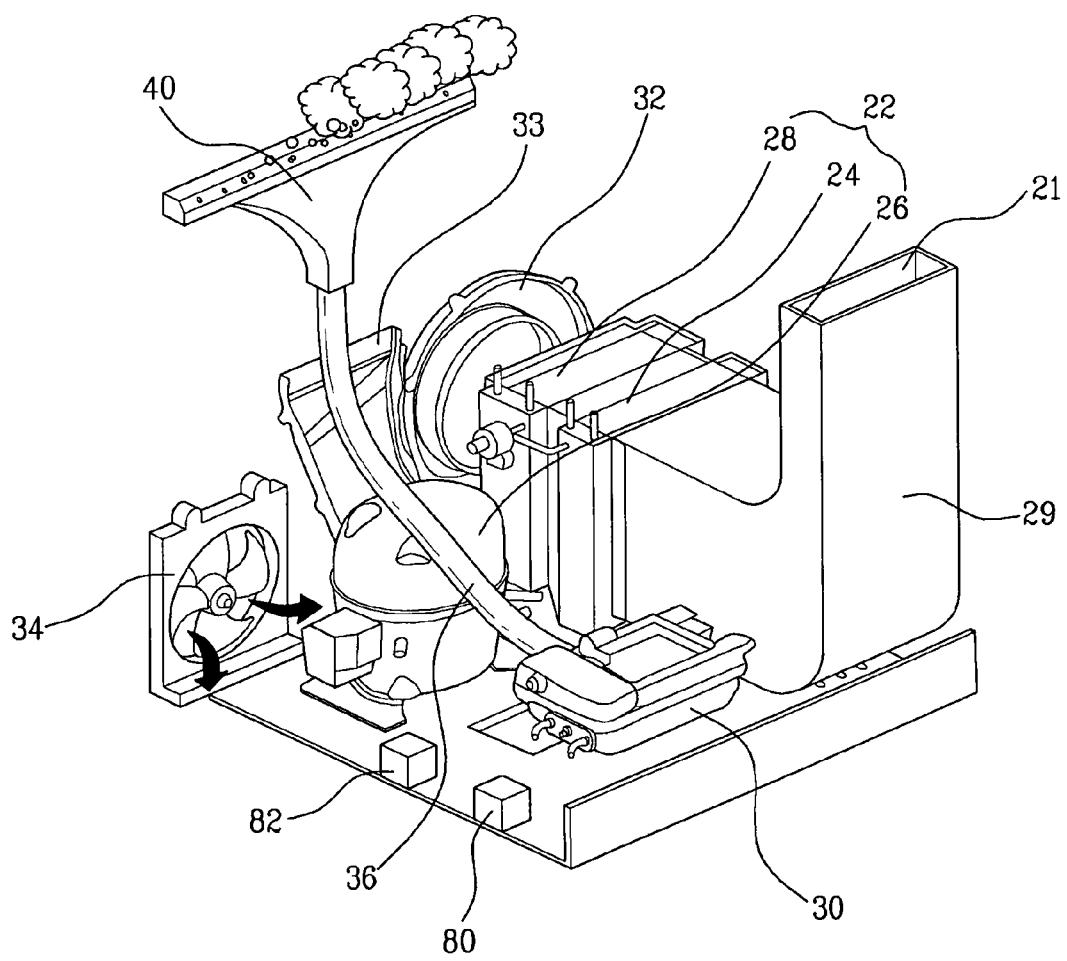
FIG. 2 is a perspective view schematically illustrating an inner structure of a mechanism compartment shown in FIG. 1.

As illustrated in FIG. 1, a laundry treating apparatus 100 according to the present invention includes a cabinet 10, a steam generator 30, a controller 80, and a memory 82 (see FIG. 2). The cabinet 10 defines an accommodating space 12 ready to receive laundry therein. The steam generator 30 selectively sprays steam into the accommodating space 12 and the controller 80 controls the steam generator 30 based on programs stored in the memory 82.

The accommodating space 12 is formed within a cabinet 10, which defines an exterior appearance of the laundry treating machine 100. A door 14 is provided to allow a user to selectively open or close the accommodating space during use. Various support structures such as a rack 16 may be provided inside the accommodating space 12 to support hanging laundry 1 or laundry placed on the rack. The general configuration for supporting the laundry 1 is known in the art to which the present invention pertains, thus the detailed description thereof will be omitted.

A mechanism compartment 20 may be formed in the cabinet 10 and may comprise the first condensing device 22 and the second condensing device 50. The mechanism compartment 20 is preferably provided under the accommodating space 12 and the first and second condensing devices 22 and 50 are positioned inside the mechanism compartment 20. The positioning of the mechanism compartment 20 below the accommodating space 12 is preferable, because the dried air supplied thereto is generally a high temperature and therefore has the natural tendency to ascend.

FIG. 2 is a perspective view schematically illustrating an inner structure of the mechanism compartment 20.

As illustrated in FIG. 2, the steam generator 30 is also positioned in the mechanism compartment 20 to supply steam to the accommodating space (12, see FIG. 1).

The introduction of steam produced by the steam generator into the accommodating space 12 may have various advantageous effects on the laundry to be treated. First, the steam may act to remove wrinkles present in the laundry placed in the accommodating space. Further, the introduction of steam may have sanitary effects on the laundry because of its high temperature. Finally, the steam may have an overall refresh effect, eliminating a fabric bulking problem. The timing of spraying steam performed by the steam generator 30 may be adjusted according to the specific circumstances and needs of the user. It is preferable, however, that the steam is sprayed before hot dry air is supplied by a hot air supply device 22, which will be described later. This is because hot air may be supplied to dry the laundry after hot steam is sprayed to the laundry.

The steam generator 30 includes a heater (not shown) and the water supplied inside the steam generator 30 is heated by the heater to generated steam to be supplied to the accommodating space 12. A water supply source supplying water to the steam generator 30 may be an external water tap or a removable container type supply (not shown) provided in the mechanism compartment 20. With the removable container type supply, the user can separate the container from the mechanism compartment 20 and fill up the container with water. Once the container has been filled appropriate, the user can re-install the container back in the mechanism compartment 20 so that it may feed a water supply to the steam generator 30.

The steam generated by the steam generator 30 may be supplied to the accommodating space 12 via a steam hose 36 and a steam nozzle 40. It is preferable to have a shorter steam hose 36 to prevent the steam passing along the steam hose 36 from decreasing in temperature or condensing. If the mechanism compartment 20 is provided under the accommodating space 12, the steam nozzle 40 may supply steam from a top of the mechanism compartment 20, which is also a bottom of the accommodating space 12.

The mechanism compartment 20 may further include a hot air supply device 22 to selectively supply hot air to the accommodating space 12. The hot air supply device 22 may dehumidify and heat air and supply the resulting dried/heated air into the accommodating space 12 to dry the laundry. The hot air supply device 22 may be an electric or gaseous type heater or a heat pump capable of dehumidifying and heating air as shown in FIG. 2. The following description will present an exemplary embodiment where a heat pump is used as the hot air supply device 22.

A heat pump 22 corresponding to the hot air supply device 22 may be similar to a heat pump used in an air conditioner. That is, the heat pump may include an evaporator 24, a compressor 26, a condenser 28, and an expansion valve (not shown). Refrigerant is then circulated through the heat pump 22 sequentially, to dehumidify and heat air. Specifically, the evaporator 24 evaporates the refrigerant flowing through it and the refrigerant absorbs latent heat from the ambient air, thus cooling the air and condensing the moisture contained therein. Then the air passes through the condenser 28. The refrigerant flowing from the compressor 26 into the condenser 28 is condensed and releases latent heat into the ambient air passing through the condenser, thus heating the ambient air. The air that is dried and heated may then be re-supplied to the accommodating space 12 once it has passed the evaporator 24 and the condenser 28.

An inlet 21 formed on a circulation duct 29 may be disposed at a top of the mechanism compartment 20 and air inside the accommodating space 12 may be drawn into the inlet 21. The circulation duct 29 connects the evaporator 24, the condenser 28, and a fan 32, and defines an air circulation flow path. The air following the circulation flow path may be drawn into the inlet 21, from the accommodating space, and may pass into the circulation duct 29. The air may then be dehumidified and heated as it passes through the heat pump 22, and then may be re-supplied to the accommodating space 12 via an outlet 33 by a fan 32.

Although not shown, a filter may be provided at the inlet 21. The filter provided at the inlet 21 may filter various foreign substances, such as lint, hair, or the like, which might be contained in the air supplied from the accommodating space. Thus, allowing only filtered air to be supplied to the circulation duct 29 and re-supplied to the accommodating space 12.

In addition, a circulation fan 34 may be provided in a rear of the mechanism compartment 20. The circulation fan 34 may blow external air into the mechanism compartment 20 to cool the heat pump 22, specifically to cool the compressor 26 of the heat pump 22. This cooling effect prevents the temperature inside the mechanism compartment 20 from increasing to undesirable levels, which may result in damage or otherwise dangerous conditions.

In order to properly treat the laundry according to this exemplary embodiment of the invention, the laundry should be exposed to an environment having a predetermined high temperature for more than a predetermined time period. The predetermined temperature and time period may be adjusted according to sanitization purposes. Where the user wishes to sanitize the laundry, a standard sanitary temperature may be approximately between 55° to 65° and a standard time may be approximately 10 minutes. Thus in order to sanitize the laundry to be treated, the temperature of the laundry treating machine may be maintained between 55°~65° for 10 minutes or more.

In case of sanitizing the laundry, it may be necessary to maintain the temperature of the laundry at a minimum standard sanitary value, and depending on the laundry load the temperature of the steam supplied should be adjusted appropriately. For example, if the laundry load is large, i.e. large volume with a high heat capacity, it may not be easy to change the temperature of the laundry with the introduction of steam. In contrast, if the laundry load is small, i.e. small volume with a low heat capacity, it may be easier to change the temperature of the laundry with the steam. Therefore, the temperature and time of the steam supplied to the accommodating space 12 should preferably be controlled in accordance with the heat capacity of the load of laundry received therein.

Figure 3:
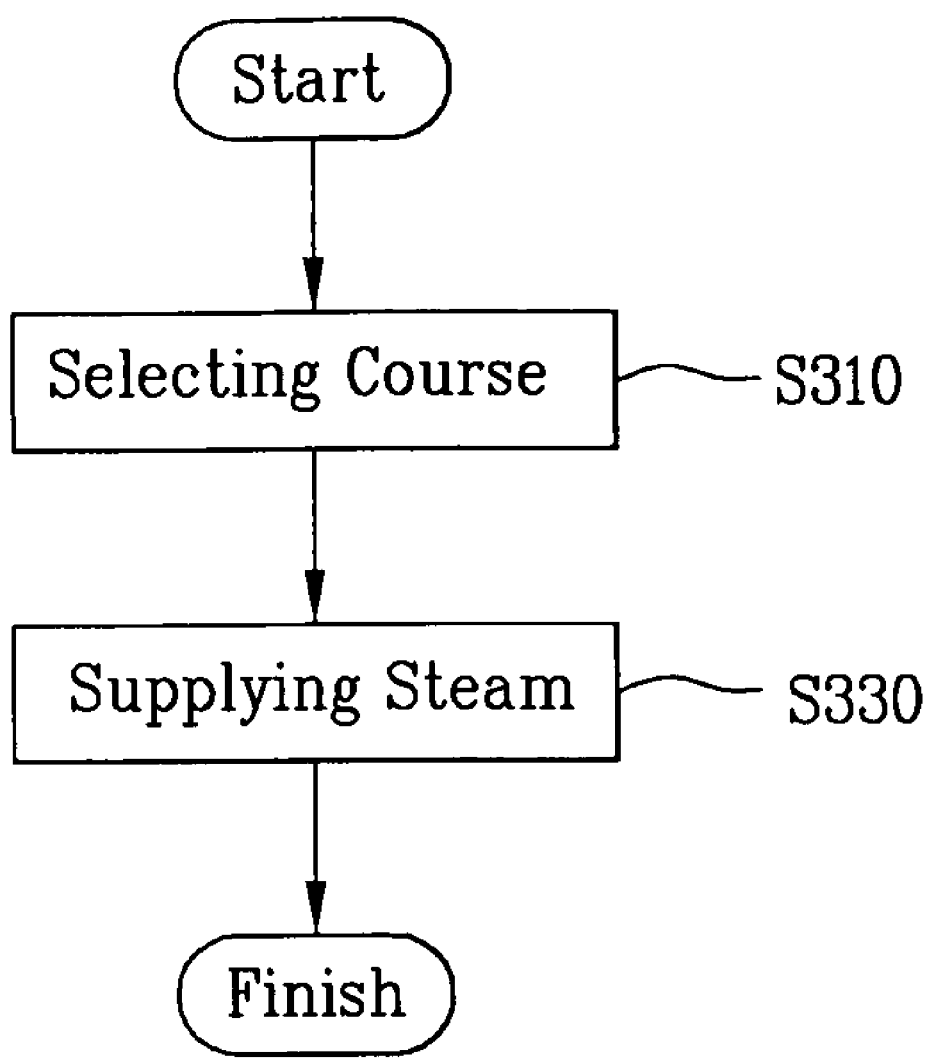
FIG. 3 is a flow chart illustrating a control method of the cloth treating apparatus according to an exemplary embodiment of the invention.

FIG. 3 is a flow chart illustrating a control method of the laundry treating machine according to an exemplary embodiment of the present invention.

As illustrated in FIG. 3, the control method of the laundry treating machine includes selecting one of at least two sanitary courses to sanitize laundry contained in the accommodating space 12 (S310). Then depending on the course, selected steam is supplied to the laundry at a predetermined temperature and time period (S330). Here, at least two courses may be preset based on a load size of the laundry. During the steam supplying step, the temperature of the steam supply may be controlled to maintain a predetermined sanitary temperature of the laundry throughout the predetermined time period.

During the use of the machine 100, the user loads the laundry into the laundry treating machine and selects a sanitary course (S310). At this time, the user may select one of the at least two sanitary courses preset in the laundry treating machine, which relate to a load amount, i.e. heat capacity of the laundry. It is also envision that the user may also have the option to select a particular type of laundry directly.

At least two sanitary courses preset in the laundry treating machine will now be described. Specifically, the at least two sanitary courses may include a first and second course. Each of the first and second courses may have a predetermined maximum temperature (T_h), a predetermined minimum temperature (T_l) of the accommodating space and a predetermined steam supply time (t). At least one of the predetermined temperatures in the first course is different from at least one corresponding predetermined temperature in the second course.

The first and second courses may be classified and programmed according to a load amount, i.e. the heat capacity of the total laundry placed in the accommodating space 12. It is noted that the first and second courses may have at least one of unique maximum temperatures, unique minimum temperatures, or unique steam supplying times.

Further, the load amounts of the first and second courses may be predetermined. For example, in an exemplary embodiment the load amount of the laundry in the first course may be preset to be substantially larger than the load amount of the laundry in the second course. If the load amount, i.e. the heat capacity of the total laundry, in the first course is larger, the laundry that would be appropriate for use with the first course may be thick and bulky laundry having a large volume and relatively higher density. If the load amount in the second course is smaller, the laundry that would be appropriate for use with the second may be thin laundry having a small volume and relatively lower density.

The predetermined maximum temperature (T_h) for the first sanitizing course (large load, high heat capacity) may be substantially higher than in the second sanitizing (small load, low heat capacity). This is due to the fact that a higher temperature may be necessary to efficiently raise the temperature of a large load of laundry having a high heat capacity. For the same reasons the steam supply time of the first course may be substantially longer than the steam supply time of the second course.

When the user selects a sanitary course, the controller 80 of the laundry treating machine controls the steam generator 30 according to the course that is selected. As a result, the temperature of the laundry may be controlled such that it is maintained at the predetermined sanitary temperature or higher.

If steam is supplied to the accommodating space according to a selected course, and the maximum temperature, the minimum temperature, and the steam supply time are adjusted, a corresponding control method may be applied differently according to the load amount of the selected course. For example, if the load amount, i.e. the heat capacity, of the laundry is large, it may be more difficult to increase the temperature of the laundry. Thus, it is preferable that the temperature of accommodating space is controlled and maintained with respect to the predetermined maximum temperature. If on the other hand, the load amount, i.e. heat capacity, of the laundry is small, the temperature of the laundry may be more easily modified. Here, it is preferable that the temperature of the accommodating space is controlled and maintained with respect to the predetermined minimum temperature or higher.

Specifically, according to the control method of the laundry treating machine of this exemplary embodiment, the first course may include at least two courses, A and B, which may be preprogrammed in accordance with a predetermined laundry load amount. The predetermined load amount of the laundry in course A may be larger than that of the laundry in the B course.

If the user selects course A in the course selecting step (S310), the controller 80 adjusts the steam supply time period according to the predetermined maximum temperature of the accommodating space. When course A is selected, the controller 80 also controls the heater of the steam generator 30 such that it shuts the heater off the first time the temperature of the accommodating space reaches the predetermined maximum temperature value.

As mentioned above, course A of the first course may correspond to a course where the laundry load amount is the largest. Given the load amount, the temperature of the laundry may not be quickly modified by the steam. If the maximum temperature value of the accommodating space is set appropriately high, the temperature of the accommodating space will reach the predetermined maximum value and the temperature of the laundry will remain at the sanitary standard value or higher (55° to 65°) even after the heater of the steam generator has been turned off.

Figure 4:
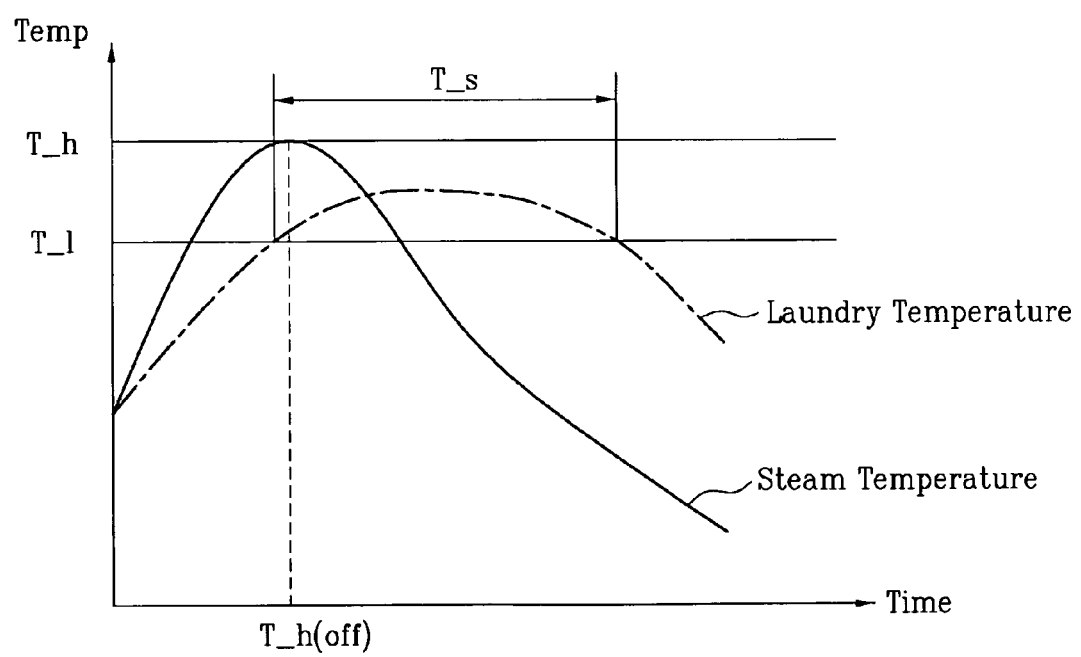
FIGS. 4, 5, and 6 are graphs illustrating temperatures of steam supplied according to selected courses in accordance with an embodiment of the disclosure.
Figure 5:
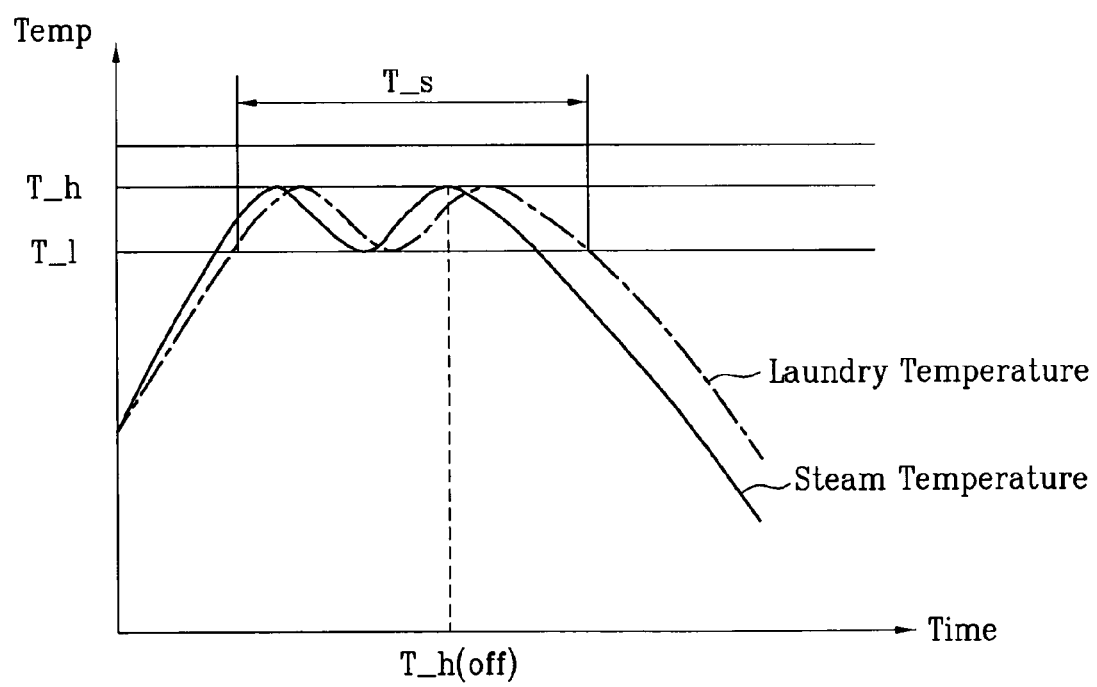

FIG. 4 is a graph illustrating the temperature changes of the accommodating space and the laundry if course A of the first course is selected. In the graph of FIG. 5, the vertical axis defines temperature increase and the horizontal axis defines time passage.

As illustrated in FIG. 4, even though the temperature of the accommodating space is increased by the supplied steam, the temperature of the laundry may not change drastically, but rather gradually. This is because the load amount, i.e. heat capacity, of the laundry in course A is large, as mentioned above. When the heater is turned off (T_h(off)), the temperature of the accommodating space may decrease drastically, while the temperature of the laundry may decrease more gradually.

The maximum temperature (T_h) of the accommodating space is appropriately set in course A. Thus, if the predetermined maximum temperature of the accommodating space is reach and then the heater of the steam generator is turned off, the temperature of the laundry may be maintained at the sanitary standard value or higher for standard sanitary time (T_s) or more. The maximum temperature of the accommodating space predetermined in course A may be adjusted according to the size of the laundry treating machine, the volume of the accommodating space, and the capacity of the hot air supply device. As a result, the maximum temperature of the accommodating space is not limited to any specific value, for example, it may be set at approximately 75° C. The minimum temperature of the accommodating space (T_l) in course A is also not limited to a specific value and may, for example, be set to be approximately between 60° C. and 70° C.

The load amount of the laundry in course B of the first course may be smaller than that of course A, but larger than that of the second. Thus, the laundry load is still relatively large and the temperature of the laundry may not be as sensitive to temperature change as compared with in the second course, which will be described in detail. Thus in course B the temperature of the laundry may be controlled relative to the predetermined maximum temperature (T_h), similar to course A, however, the heater of the steam generator is turned off if the temperature of the accommodating space reaches the highest value (T_h) for a second time. In this respect, course B is different from course A.

Specifically, the laundry in course B may be more sensitive to temperature change than the laundry in course A, but less sensitive to temperature change than the laundry in the second course. If the B course is selected and the temperature of the accommodating space is increased, the temperature of the laundry may be also increased according to the temperature of the accommodating space. Similarly, if the heater is turned off and the temperature of the accommodating space decreases, the temperature of the laundry may decrease accordingly.

As soon as the B course is selected and the temperature of the accommodating space reaches the predetermined maximum value for the first time, the heater is completely turned off, like in the A course. The temperature of the laundry may then decrease relatively fast, compared with course A. This relatively quick decrease in temperature may have the result that the laundry is not maintained at the standard sanitary temperature or higher for a long enough time to properly sanitize the clothing. In order to obviate this result, course B provides that the heater is turned off completely only after the temperature of the accommodating space reaches the predetermined maximum value for the second time.

FIG. 5 is a graph illustrating temperatures of the accommodating space and the laundry in the B course. As illustrated in FIG. 5, if the temperature of the accommodating space reaches the predetermined maximum value (T_h) for the first time, the controller 80 turns off the heater only temporarily for a predetermined period of time to prevent the temperature of the laundry from rising too high. The heater is then turned on again to prevent the temperature of the laundry from dropping below the sanitary standard value too soon. Then once the temperature of the accommodating space reaches the predetermined maximum value for the second time, the heater is completely turned off. In this case, the temperature of the laundry may decrease gradually such that it is maintained at the predetermined sanitary standard value or higher for a predetermined period of time.

In this case, the maximum temperature of the accommodating space in course B may be adjusted depending on the size of the laundry treating machine, the volume of the accommodating space, and the capacity of the hot air supply device. Thus, the maximum temperature of the accommodating space in the B course is not limited to a specific value. For example, the maximum temperature may be set approximately at 70° C. and the minimum temperature of the accommodating space in course B may be set approximately between 60° C. and 65° C.

The user may also select the second course in the course selecting step (S310). If the second course is chosen, the controller 80 may adjust the steam supplying time according to the predetermined minimum temperature. Specifically, if the second course is selected, the controller 80 may maintain the temperature of the accommodating space at the standard sanitary temperature or higher for the predetermined standard sanitary time, and may also completely turn off the heater.

The laundry load amount of the second course is less than the load amount of the first course, and accordingly it has a lower heat capacity. With a lower heat capacity, the laundry will be more sensitive to temperature changes of the accommodating space. As a result, if the second course is selected, the minimum temperature of the accommodating space may be set as a sanitary standard temperature, for example, approximately at 60°. The temperature of the accommodating space is then feedback-controlled to be at the predetermined minimum temperature of the accommodating space or higher.

In the second course, since the smaller load is more responsive to temperature change, if steam is supplied toward the laundry the temperature of the accommodating space may be maintained at the sanitary standard temperature or higher. If the time period for which the temperature of the accommodating space is maintained at the sanitary standard temperature or higher is the sanitary standard time or longer, it can be expected that the temperature of the laundry may be maintained at the sanitary standard temperature or higher for the sanitary standard time or longer. Thus, in the second course it is preferable that the predetermined minimum temperature of the accommodating space is approximately the same as the sanitary standard temperature.

Figure 6:
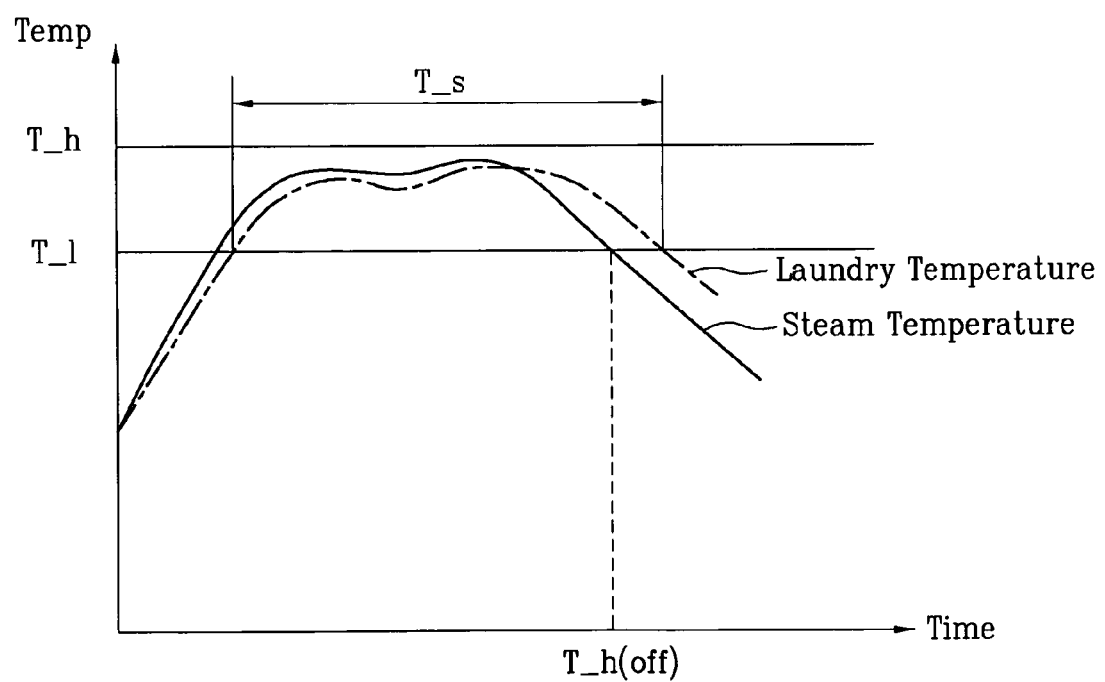

FIG. 6 is a graph illustrating temperatures of the accommodating space and the laundry if the second course is selected.

As illustrated in FIG. 6, the temperature of the laundry in the second course may change quite responsively to the changing temperature of the accommodating space. The controller 80 feedback-controls the temperature of the accommodating space to be at the predetermined minimum temperature of the accommodating space (T_l) or higher, that is, the sanitary standard temperature or higher. Hence, if the time period for which the temperature of the accommodating space is maintained at the predetermined minimum temperature or higher is the sanitary standard time or longer, the controller 80 may turn off the heater (T_h(off)). Therefore, the temperature of the laundry may be maintained to be at the sanitary standard temperature or higher for the sanitary standard time or longer.

The specific control method of the laundry treating machine is similar to the above control methods described above and the detailed description thereof will be omitted.

As mentioned above, according to the control method of the present invention, steam may be supplied appropriately according to the load amount of the laundry treating machine such that damage to the fabric of the laundry may be prevented, while still sanitizing or sterilizing the laundry.

Furthermore, according to the present invention, steam may be supplied according to the load amount such that energy loss of the laundry treating machine may be reduced as much as possible.

It will be apparent to those skilled in the art that various modifications and variations can be made in the present invention without departing from the spirit or scope of the inventions. Thus, it is intended that the present invention covers the modifications and variations of this invention provided they come within the scope of the appended claims and their equivalents.

What is claimed is:

1. A control method of a laundry treating machine comprising an accommodating space receiving laundry therein, the control method comprising:
   selecting one of at least a first or second courses to sanitize laundry; and
   supplying steam to the laundry in the accommodating space;
   controlling a temperature of the accommodating space and a steam supplying time by supplying the steam to the accommodating space, in accordance with the selected course; and
   maintaining a temperature of the laundry at a predetermined standard sanitary temperature or higher for a predetermined standard sanitary time, in accordance with the selected course by controlling a heater generating steam to adjust the steam supplying time according to the predetermined maximum temperature of the accommodating space in the first course and the predetermined minimum temperature of the accommodating space in the second course.

2. The control method of claim 1, wherein selecting one of the first or second courses is based on one of a plurality of preset sanitary courses or based on the type of laundry.

3. The control method of claim 1, wherein at least one of a predetermined maximum temperature of the accommodating space, a predetermined minimum temperature of the accommodating space, and the steam supplying time in the second course is different from a corresponding one in the first course.

4. The control method of claim 3, wherein a laundry load amount in the first course is different from a laundry load amount in the second course.

5. The control method of claim 4, wherein the laundry load amount in the first course is substantially larger than the laundry load amount in the second course, and the predetermined maximum temperature of the accommodating space in the first course is substantially higher than the predetermined maximum temperature of the accommodating space in the second course.

6. The control method of claim 5, wherein the steam supplying time in the first course is substantially longer than the steam supplying time in the second course.

7. The control method of claim 3, further comprising:
   controlling the temperature of the accommodating space according to the predetermined maximum temperature of the accommodating space if the first course is selected; and
   feed-back controlling the temperature of the accommodating space to maintain the temperature of the accommodating space between the predetermined maximum temperature and the predetermined minimum temperature of the accommodating space if the second course is selected.

8. The control method of claim 7, further comprising controlling the temperature of the accommodating space by turning on or off the heater generating steam.

9. The control method of claim 8, the first course comprising at least course A and course B, the control method further comprising:
   selecting one of course A or course B;
   turning off the heater completely if the temperature of the accommodating space reaches the predetermined maximum temperature for a first time if course A is selected; and
   turning off the heater temporarily if the temperature of the accommodating space reaches the predetermined maximum temperature a first time, then turning off the heater completely if the predetermined maximum temperature is reached for a second time if course B is selected.

10. The control method of claim 8, further comprising selecting the second course;
   feedback-controlling temperature of the accommodating space to maintain the temperature of the accommodating space between the predetermined maximum temperature and the predetermined minimum temperature of the accommodating space; and
   turning off the heater if a time period for which the temperature of the accommodating space is maintained at the predetermined minimum temperature of the accommodating space or higher is equal to or greater than the standard sanitary time.

11. The control method of claim 1, the first course comprising at least course A and course B, the control method further comprising:

selecting one of course A or course B depending on the laundry load amount, and turning off the heater generating steam completely if the temperature of the accommodating space reaches the predetermined maximum temperature for a first time if course A is selected; and turning off the heater generating steam temporarily if the temperature of the accommodating space reaches the predetermined maximum temperature a first time, then turning off the heater completely if the predetermined maximum temperature is reached for a second time if course B is selected.

12. The control method of claim 1, further comprising selecting the second course;

feedback-controlling the temperature of the accommodating space to maintain the temperature of the accommodating space between the predetermined maximum temperature and the predetermined minimum temperature of the accommodating space; and turning off the heater generating steam if a time period for which the temperature of the accommodating space is maintained at the predetermined minimum temperature of the accommodating space or higher is equal to or greater than the standard sanitary time.

* * * * *